United States Patent
Okazaki et al.

(10) Patent No.: US 6,329,443 B1
(45) Date of Patent: Dec. 11, 2001

(54) ACRYLATES AND ACTINIC RADIATION-CURABLE COMPOSITIONS CONTAINING THEM

(75) Inventors: Eiichi Okazaki; Tetsuji Jitsumatsu, both of Nagoya (JP)

(73) Assignee: Toagosei CO, Ltd., Tokyo (JP)

( * ) Notice: Subject to any disclaimer, the term of this patent is extended or adjusted under 35 U.S.C. 154(b) by 0 days.

(21) Appl. No.: 09/446,370

(22) PCT Filed: Jun. 19, 1998

(86) PCT No.: PCT/JP98/02737

§ 371 Date: Dec. 20, 1999

§ 102(e) Date: Dec. 20, 1999

(87) PCT Pub. No.: WO98/58912

PCT Pub. Date: Dec. 30, 1998

(30) Foreign Application Priority Data

Jun. 20, 1997 (JP) .................................................. 9-180614

(51) Int. Cl.[7] ........................................................ C08F 2/46
(52) U.S. Cl. .................. 522/176; 522/173; 522/166; 522/164; 522/150; 522/151; 522/152; 522/167; 522/182; 522/134; 522/142; 522/145
(58) Field of Search ..................................... 522/167, 152, 522/150, 151, 164, 166, 173, 176, 182, 134, 142, 145

(56) References Cited

U.S. PATENT DOCUMENTS

| 4,626,497 | * | 12/1986 | Roth et al. | 430/293 |
| 4,686,166 | | 8/1987 | Kumagai et al. | 430/109 |
| 5,006,621 | | 4/1991 | Wahle et al. | 526/262 |
| 5,523,152 | | 6/1996 | Thurber et al. | 428/323 |
| 5,580,647 | | 12/1996 | Larson et al. | 428/245 |

FOREIGN PATENT DOCUMENTS

| 61-156145 | 7/1986 | (JP) . |
| 62-081643 | 4/1987 | (JP) . |
| 62-205108 | 9/1987 | (JP) . |
| 01-242569 | 9/1989 | (JP) . |
| 03-068609 | 3/1991 | (JP) . |
| 6-27659 | 2/1994 | (JP) . |

* cited by examiner

Primary Examiner—James J. Seidleck
Assistant Examiner—Sanza McClendon
(74) Attorney, Agent, or Firm—Fitch, Even, Tabin & Flannery

(57) ABSTRACT

New imido(meth) acrylates of general formula (1), wherein $R_1$, $R_2$ and $R_3$ may be the same or different and each represents H or $CH_3$; $R_4$ to $R_7$ may be the same or different and each represents H or $C_mH_{2m+1}$ (in which m is 1 to 6); and n represents 1 to 4, and radiation-curable compositions prepared from them, easily cured by the irradiation with radiations, particularly ultraviolet rays, to form cured compositions excellent in weather resistance, abrasion resistance and adhesion to a base, and free from the problem of odor.

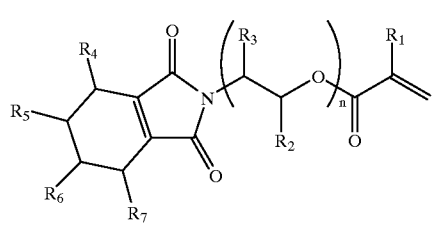

(1)

6 Claims, No Drawings

ACRYLATES AND ACTINIC RADIATION-CURABLE COMPOSITIONS CONTAINING THEM

This application is the national phase of international application PCT/JP98/02737 filed Jun. 19, 1998 which designated the U.S.

TECHNICAL FIELD

The present invention relates to new acrylates and compositions which comprise the acrylates and are curable by irradiation with radiations such as electron rays and ultraviolet rays, namely, radiation-curable compositions. Since coating films or molded articles can be derived from the compositions and are excellent in weather resistance and abrasion resistance, the compositions of the present invention can be utilized as coating agents, adhesives and molding materials. That is, the present invention belongs to paints, adhesives and plastic molding technique.

BACKGROUND ART

Due to their rapid curability, for radiation-curable compositions, energy and time required for drying can be much reduced as compared with the conventional solvent type resin compositions, and, in addition, drying apparatuses are not needed. Thus, saving of spaces can be attained. Furthermore, the compositions require only a small amount of solvents or require no solvents. For these reasons, they are used in a yearly increased amount as materials safe for earth environment.

Moreover, recently, the radiation-curable compositions expand in their use to various fields, but performances required in these fields sometimes cannot be attained by only the combination of oligomers or monomers conventionally used as starting materials.

On the other hand, molded articles made from polymethyl methacrylate resins, polycarbonate resins, etc. have various advantages such as light weight and excellent shock resistance and, easy processing, and are used in many fields. However, since these plastic molded articles are insufficient in abrasion resistance of the surface, their surface is apt to be damaged and improvement in abrasion resistance is demanded. Furthermore, these molded articles are sometimes used outdoors such as automobile parts, and are also strongly demanded to have weather resistance.

In order to improve abrasion resistance, methods of coating the surface of these plastic molded articles with ultraviolet-curable compositions have been investigated. However, these compositions are sometimes insufficient in abrasion resistance and adhesiveness to plastics, and even if these performances are satisfied to some extent, in many cases, there are problems in weather resistance.

That is, in the case of ultraviolet-curable compositions mainly composed of acrylates, which are in most cases used as radiation-curable compositions, photopolymerization initiators that generate active radicals by the irradiation with ultraviolet rays must be added to the compositions for curing them with ultraviolet rays. However, the photopolymerization initiators remain in cured products of the compositions and deteriorate weather resistance of the cured products to cause coloration or discoloration, peeling of coat and cracking. Therefore, the ultraviolet-curable compositions are unsatisfactory for the use requiring weather resistance. Further, decomposition products of photopolymerization initiators in the cured products sometimes give odor to the cured products.

Furthermore, it has been attempted to improve weather resistance of the compositions by adding weather resistance improvers such as ultraviolet absorbers, light stabilizers and antioxidants, but the effect is still insufficient and, besides, there are problems that the weather resistance improvers hinder the curing reaction to cause deterioration in ultraviolet-curability of the compositions and result in reduction of productivity.

Recently, it has been found that N-substituted maleimide compounds have a function as photopolymerization initiators, and it has been reported that vinyl ether or an acrylate is polymerized by ultraviolet rays without using photopolymerization initiators [Sonny Jonsson et al, Radotech 95 Europe, Previous Lecture Manuscripts "Academic Day", page 34].

This function of N-substituted maleimide compounds to initiate photopolymerization is excellent, being different from conventional photopolymerization initiators, but since these maleimide compounds are solid and high in melting point, they are difficult to handle, and, furthermore, they must be dissolved in acrylates in order to use them in the form of liquid. However, maleimide compounds are sometimes low in solubility in acrylates, and, in this case, if the amount of maleimide compounds is increased, they are precipitated. Due to these problems, only curable compositions of limited formulations can be produced, and when formulations of compositions are changed depending on the properties demanded in various uses, the compositions do not satisfy the desired properties.

In addition, these maleimide compounds are low-molecular weight compounds, and when they are added to curable compositions as a component having a function as photopolymerization initiators, if they remain without being bonded to the cured products, characteristics of the cured products are deteriorated.

Furthermore, these maleimide compounds are generally produced by addition reaction of maleic anhydride with amines and the subsequent dehydration reaction, but this method produces them in low yields owing to side reaction of unsaturated group of the starting maleic anhydride. A method of production with protecting the unsaturated group was proposed (JP-A-2-268155), but a step of deprotection reaction is added and the production is not simple.

Based on the above facts, the inventors have conducted an intensive research in an attempt to find a curable composition which is easy in preparation of its starting materials, is easily curable by irradiation with radiations, especially ultraviolet rays, provides cured products excellent in weather resistance and abrasion resistance, has no problem of odor, and is excellent in adhesion to substrate.

DISCLOSURE OF INVENTION

As a result of various investigations conducted by the inventors, it has been found that a novel N-substituted maleimide compound, namely, imido (meth)acrylate, solves the above problems. Thus, the present invention has been accomplished.

That is, the present invention relates to an imido acrylate represented by the following formula (1).

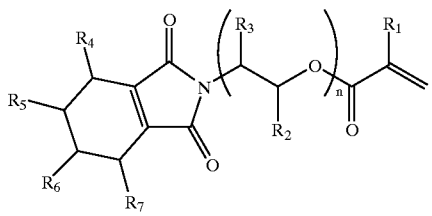

(1)

[wherein $R_1$, $R_2$ and $R_3$ each represents H or $CH_3$, and $R_1$, $R_2$ and $R_3$ in one molecule may be the same or different, $R_4$–$R_7$ each represents H or $C_mH_{2m+1}$ (m=1–6), and $R_4$–$R_7$ in one molecule may be the same or different, and n=1–4].

Especially, the present invention relates to an imido (meth)acrylate with $R_3$–$R_7$ in the above formula being H, which is represented by the following formula (2).

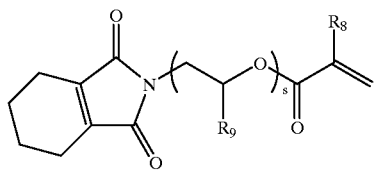

(2)

[wherein $R_8$ and $R_9$ each represents H or $CH_3$ and $R_8$ and $R_9$ in one molecule may be the same or different, and s=1–4].

Moreover, the present invention relates to a polymer having the above imido acrylate or the above imido acrylate and other compound having an ethylenically unsaturated bond as constitutive monomer units.

In addition, the present invention relates to a radiation-curable composition having the above imido acrylate or polymer as an effective component.

The present invention will be explained in detail below.

In this specification, for assurance of accuracy, acrylate and methacrylate, acrylic acid and methacrylic acid, and acryloyl group and methacryloyl group are called (meth)acrylate, (meth)acrylic acid, and (meth)acryloyl group, respectively.

Imido (meth)Acrylate

The imido (meth)acrylates of the present invention are compounds represented by the above formula (1).

When m exceeds 6 in $R_4$–$R_7$, curability of the compositions is deteriorated, and strength of the cured products is also reduced. When n exceeds 4, concentration of imido site in the molecule decreases to cause deterioration of curability. Thus, they are not suitable for obtaining the desired radiation-curable compositions of the present invention.

Among the above imido (meth)acrylates, preferred are those represented by the formula (2) which correspond to the compounds represented by the formula (1) where $R_3$–$R_7$ are H because the resulting compositions are excellent in curability and the cured products are excellent in strength.

The imido (meth)acrylates of the present invention are easily cured with radiations, and even when they are cured with ultraviolet rays, photopolymerization initiators are not needed in most cases, and even in the case of needing the photopolymerization initiators, they are cured at practically sufficient curing speed with use of a small amount of the initiators, and the cured products have practically sufficient properties and are excellent in weather resistance.

The imido (meth)acrylates of the present invention can be produced through one step, and can be easily obtained by dehydration condensation reaction of an N-hydroxyalkyltetrahydrophthalimide derivative with (meth)acrylic acid.

In more detail, there may be mentioned a method which comprises dissolving an N-hydroxyalkyltetrahydrophthalimide derivative, (meth)acrylic acid and an acid catalyst in an organic solvent such as toluene, followed by stirring with heating.

The acid catalysts include sulfuric acid, p-toluenesulfonic acid, etc. Amount of the acid catalyst can be optionally set depending on the starting materials used, but is preferably 0.1–5% by weight in the reaction mixture. Reaction temperature can also be optionally set depending on the starting materials used, but is preferably 60–150° C. This reaction is a dehydration reaction, and water produced in the reaction is preferably removed from the reaction system. Thus, the reaction temperature is more preferably the boiling point or higher of the solvent used. In this case, in order to inhibit the polymerization of the resulting imido (meth)acrylate, it is preferred to add a polymerization inhibitor such as hydroquinone monomethyl ether.

Furthermore, the N-hydroxyalkyltetrahydrophthalimide used as a starting material in this production method can be prepared through one step by the addition reaction of a 3,4,5,6-tetrahydrophthalic anhydride derivative with an amino alcohol and the subsequent dehydration reaction without protection of the unsaturated bond, and the reaction quantitatively proceeds. As an example of the method, mention may be made of a method which comprises dissolving a 3,4,5,6-tetrahydrophthalic anhydride derivative and an amino alcohol in an organic solvent such as toluene, followed by stirring with heating. The reaction proceeds without addition of a particular catalyst, but, if necessary, sulfuric acid, p-toluenesulfonic acid, etc. can be added. Reaction temperature can be optionally set depending on the starting materials used, but is preferably 60–150° C. This reaction is a dehydration reaction, and water produced in the reaction is preferably removed from the reaction system. Thus, the reaction temperature is more preferably the boiling point or higher of the solvent used.

Since the imido (meth)acrylate of the present invention is a compound having a cyclohexyl ring and a (meth)acryloyl group, it is also excellent in solubility in (meth)acrylates, and cured products have a proper hydrophobic property due to the cyclohexyl group resulting from the starting imido (meth)acrylate and, hence, are excellent in weather resistance, especially weather resistance under high humidity conditions. Furthermore, since the imido group unit of the imido (meth)acrylate is of high polarity, the cured film is excellent in adhesion to various synthetic resin molded articles and the cured products are excellent in abrasion resistance and weather resistance.

The imido (meth)acrylates can also be prepared by the methods disclosed in the following literatures and patents.

Kiyoshi Kato et al, "Journal of Synthetic Organic Chemistry Association", 30 (10), 897, (1972).

Javier de Abajo et al, "Polymer", vol.33 (5), (1992).

JP-A-56-53119

JP-A-1-242569

Polymers Having Imido (meth)Acrylates as Constitutive Monomer Units

The imido (meth)acrylates of the present invention can be made into curable polymers (hereinafter referred to as "imido polymers") by homopolymerization or copolymerization with compounds having an ethylenically unsaturated double bond, and the polymers can also be used as starting materials for the radiation-curable compositions.

The imido polymers have the same maleimido groups as of the above imido (meth)acrylates. Therefore, they are easily cured with radiation like the imido (meth)acrylates, and even when they are cured with ultraviolet rays, photopolymerization initiators are not needed in most cases, and even in the case of needing the photopolymerization initiators, they are cured at practically sufficient curing speed with use of a small amount of the initiators, and the cured products have practically sufficient properties and are excellent in weather resistance.

As the compounds having an ethylenically unsaturated double bond and copolymerizable with the imido (meth) acrylates, mention may be made of, for example, aromatic compounds having an ethylenically unsaturated double bond, such as styrene and α-methylstyrene, unsaturated carboxylic acids such as (meth)acrylic acid, crotonic acid and cinnamic acid, dimers or higher oligomers which are Michael addition reaction products of unsaturated carboxylic acids, (meth)acrylonitrile, vinyl acetate, and (meth) acrylates. Specific examples of the (meth)acrylates are alkyl (meth)acrylates such as methyl (meth)acrylate, ethyl (meth) acrylate, butyl (meth)acrylate, isobutyl (meth)acrylate, and 2-ethylhexyl (meth)acrylate; alicyclic alkyl (meth)acrylates such as cyclohexyl (meth)acrylate; substituted aryl (meth) acrylates such as benzyl (meth)acrylate; alkoxy (meth) acrylates such as 2-methoxyethyl (meth)acrylate and 2-ethoxyethyl (meth)acrylate; isobornyl (meth)acrylate; hydroxyalkyl (meth)acrylates such as hydroxyethyl (meth) acrylate and hydroxypropyl (meth)acrylate; and carboxyl group-containing (meth)acrylates such as ω-carboxypolycaprolactone mono(meth)acrylate, phthalic acid monohydroxyethyl (meth)acrylate and succinic acid monohydroxyethyl (meth)acrylate.

Number-average molecular weight of the imido polymers is preferably 500–500,000, more preferably 1,000–100,000, especially preferably 1,000–50,000. The number-average molecular weight and weight-average molecular weight in the present invention are those which are obtained by calculating by polystyrene standard from the molecular weights measured by gel permeation chromatography (hereinafter referred to as "GPC") using tetrahydrofuran as a solvent.

More preferred imido polymers are homopolymers of the imido (meth)acrylate represented by the formula (2) or copolymers of the imido (meth)acrylate with an alkyl (meth) acrylate which have alkyl groups having 1–8 carbon atoms or styrene, which have a number-average molecular weight of 1,000–100,000, preferably 1,000–50,000.

The constitutional proportion of the monomers in the copolymer is imido (meth)acrylate: alkyl (meth)acrylate=1-9:9-1 in molar ratio in the case of the alkyl (meth)acrylate which have alkyl groups having 1–8 carbon atoms, and imido (meth)acrylate:styrene=2-5:8-5 in molar ratio in the case of styrene.

The imido polymers can be produced by various processes and by polymerizing the starting monomers in accordance with conventional polymerization processes such as solution polymerization, emulsion polymerization and suspension polymerization. Among them, solution polymerization is preferred because no emulsifiers are needed and the resulting polymers are excellent in weather resistance.

A specific process of the solution polymerization comprises dissolving the starting monomer in an organic solvent and adding a thermal polymerization initiator thereto, followed by stirring with heating. In this case, if necessary, a chain transfer agent may be used for controlling the molecular weight of the polymers.

The organic solvents include benzene, toluene, ethyl acetate, methanol, dimethylformamide, etc.

The thermal polymerization initiators include peroxides, azo compounds and redox initiators which generate radical species by heat. Examples of the peroxides are benzoyl peroxide, lauroyl peroxide, cumene hydroperoxide, t-butyl hydroperoxide and dicumyl peroxide. Examples of the azo compounds are azobisisobutyronitrile and azobis-2,4-dimethylvaleronitrile. Examples of the redox initiators are hydrogen peroxide-iron (II) salt, peroxodisulfate-sodium hydrogensulfite and cumene hydroperoxide-iron (II) salt. Amount of the thermal polymerization initiators can be optionally set depending on the starting monomers used and molecular weight of the desired polymers, and is preferably 0.01–5% by weight in the reaction mixture. The chain transfer agents include dodecyl mercaptan, disulfide xanthate, diazothioether, 2-propanol, etc.

Reaction temperature can be set depending on the starting monomers used, the thermal polymerization initiators used and molecular weight of the desired polymers, and is preferably 50–150° C.

Radiation-curable Compositions:

The imido (meth)acrylates and imido polymers of the present invention have curability, but in order to obtain excellent radiation-curable compositions using them, it is preferred to use the following (meth)acrylates (hereinafter referred to as merely "(meth)acrylates") in combination with them.

Contents of the imido (meth)acrylate and the imido polymer in the radiation-curable composition in the case of using the (meth)acrylate in combination are preferably 5–95% by weight, more preferably 5–50% by weight. If the content of the imido (meth)acrylate or the imido polymer is less than 5% by weight, curability is inferior or strength of the cured products is insufficient, and if it is more than 95% by weight, hardness, tensile strength and abrasion resistance of the cured products are insufficient.

(Meth)Acrylates:

The (meth)acrylates used together with the imido (meth) acrylates or the imido polymers in the present invention may be any of those which are classified into monomers and oligomers.

The oligomers include urethane (meth)acrylate, polyester (meth)acrylate, epoxy (meth)acrylate, etc.

The monomers include hydroxyalkyl (meth)acrylates such as 2-hydroxyethyl (meth)acrylate and 2-hydroxypropyl (meth)acrylate; acrylates of alkylene oxide adducts of phenol such as phenoxyethyl (meth)acrylate, and halogen-aromatic nucleus substitution products thereof; mono- or di (meth)acrylates of glycol such as mono- or di (meth)acrylate of ethylene glycol, mono(meth)acrylate of methoxyethylene glycol, mono- or di (meth)acrylates of tetraethylene glycol and mono- or di(meth)acrylates of tripropylene glycol; di- or tri(meth)acrylates of alkylene oxide adducts of isocyanuric acid; and (meth)acrylates of polyols such as trimethylolpropane tri(meth)acrylate, pentaerythritol tri(meth)acrylate, pentaerythritol tetra(meth)acrylate and dipentaerythritol hexa(meth)acrylate and (meth)acrylates of alkylene oxide adducts of these polyols. Here, the alkylene oxide includes, for example, ethylene oxide and propylene oxide.

The urethane (meth)acrylate oligomers include, for example, reaction products obtained by reacting hydroxyl group-containing (meth)acrylates with reaction products of polyols and organic polyisocyanates. The polyols here include low-molecular weight polyols, polyethylene glycols, polyester polyols, etc. As the low-molecular weight polyols, mention may be made of ethylene glycol, propylene glycol, cyclohexanedimethanol, 3-methyl-1,5-pentanediol, etc. As the polyether polyols, mention may be made of polyethylene glycol, polypropylene glycol, etc. As the polyester polyols, mention may be made of reaction products of these low-molecular weight polyols or/and polyether polyols with acid components, e.g., dibasic acids such as adipic acid, succinic acid, phthalic acid, hexahydrophthalic acid and terephthalic acid or anhydrides thereof. As the organic polyisocyanates, mention may be made of tolylene diisocyanate, 4,4'-diphenylmethane diisocyanate, 4,4'-dicyclohexylmethane diisocyanate, hexamethylene diisocyanate, isophorone diisocyanate, etc. As the hydroxyl group-containing (meth) acrylates, mention may be made of hydroxyalkyl (meth) acrylates such as 2-hydroxyethyl (meth)acrylate and 2-hydroxypropyl (meth)acrylate.

The polyester (meth)acrylate oligomers include dehydration condensates of polyester polyols with (meth)acrylic acid. As the polyester polyols, mention may be made of reaction products of the low-molecular weight polyols such as ethylene glycol, polyethylene glycol, cyclohexanedimethanol, 3-methyl-1,5-pentanediol, propylene glycol, polypropylene glycol, 1,6-hexanediol and trimethylolpropane and polyols such as alkylene oxide adducts thereof with acid components, e.g., dibasic acids such as adipic acid, succinic acid, phthalic acid, hexahydrophthalic acid and terephthalic acid or anhydrides thereof.

The epoxy acrylates are those obtained by addition reaction of epoxy resins with (meth)acrylic acid, and include (meth)acrylate of bisphenol A epoxy resin, (meth)acrylate of phenol or cresol novolak epoxy resin, (meth)acrylic acid adducts of diglycidyl ether of polyether, etc.

Among these (meth)acrylates, those which have two or more (meth)acryloyl groups in one molecule are preferred because the resulting cured products are excellent in hardness and abrasion resistance. Moreover, use of aliphatic or alicyclic compounds as the (meth)acrylates is preferred because they are superior to compounds having aromatic ring in weather resistance and curability.

Photopolymerization Initiators:

The compositions containing the imido (meth)acrylate or imido polymer of the present invention are cured by irradiation with radiations, and are surely cured even with ultraviolet rays without using photopolymerization initiators, but for further improvement of curability, photopolymerization initiators can be added as far as weather resistance is not damaged.

Examples of the photopolymerization initiators are benzoins such as benzoin, benzoin methyl ether, benzoin ethyl ether and benzoin isopropyl ether, and their alkyl ethers; acetophenones such as acetophenone, 2,2-dimethoxy-2-phenylacetophenone, 2,2-diethoxy-2-phenylacetophenone, 1,1-dichloroacetophenone, 1-hydroxyacetophenone, 1-hydroxycyclohexylphenyl ketone, and 2-methyl-1-[4-(methylthio)phenyl]-2-morpholino-propane-1-one; anthraquinones such as 2-methylanthraquinone, 2-ethylanthraquinone, 2-tert-butylanthraquinone, 1-chloroanthraquinone and 2-amylanthraquinone; thioxanthones such as 2,4-dimethylthioxanthone, 2,4-diethylthioxanthone, 2-chlorothioxanthone and 2,4-diisopropylthioxanthone; ketals such as acetophenonedimethylketal and benzildimethylketal; benzophenones such as benzophenone; and xanthones.

These photopolymerization initiators can be used each alone or in combination with photopolymerization initiation accelerators such as of benzoic acid type and amine type.

Amount of these photopolymerization initiators is preferably 5 parts by weight or less, more preferably 2 parts by weight or less based on 100 parts by weight of the composition.

Weather Resistance Improvers:

At least one weather resistance improver selected from ultraviolet absorbers, light stabilizers and antioxidants can be added to the compositions containing the imido (meth) acrylate of the present invention and the compositions containing the imido polymer for the purpose of further improvement of weather resistance.

Examples of the ultraviolet absorbers are benzotriazole ultraviolet absorbers such as 2-(5-methyl-2-hydroxyphenyl) benzotriazole and 2-(3,5-di-t-amyl-2-hydroxyphenyl) benzotriazole.

The light stabilizers include hindered amine and benzoate light stabilizers. Examples of the hindered amine light stabilizers are bis(1,2,2,6,6-pentamethyl-4-piperidinyl) sebacate and bis(1,2,2,6,6-pentamethyl-4-piperidyl) 2-(3,5-di-t-butyl-4-hydroxybenzyl)-2-n-butylmalonate. Examples of the benzoate light stabilizers are 2,4-di-t-butylphenyl-3, 5-di-t-butyl-4-hydroxy benzoate.

Examples of the antioxidants are hindered phenol antioxidants such as triethylene glycol-bis[3-(3-t-butyl-5-methyl-4-hydroxyphenyl)propionate] and 1,6-hexanediol-bis[3,5-di-t-butyl-4-hydroxyphenyl]propionate].

Preferred amount of the weather resistance improvers is 0.01–5 parts by weight based on 100 parts by weight of the composition. If the amount is less than 0.01 part by weight, the effect of adding the weather resistance improver is not obtained, and if it exceeds 5 parts by weight, sometimes curability of the composition lowers or abrasion resistance of the cured products of the composition lowers.

Method of Use:

The composition of the present invention can be used for various uses such as paints and other coating agents, printing inks, adhesives, fillers, and molding materials. Especially, since the imido group site of the constitutive imido (meth) acrylate is high in polarity, the composition is excellent in adhesion to various plastics and furthermore in abrasion resistance and weather resistance, and thus the composition can be used more preferably for hard coats of plastics and molding materials because of the excellent abrasion resistance and weather resistance.

As for the method of use of the composition according to the present invention, there may be employed, for example, a general method which comprises coating the composition on a substrate by conventional coating method, followed by irradiating with radiations such as ultraviolet rays and electron rays to cure the coat in the case of the uses as coating agents, printing inks and adhesives, and a general method which comprises pouring the composition into a given frame, followed by irradiating with radiations to cure the composition in the case of uses as fillers and molding materials. As the irradiation method of radiations, there may be also employed general method known as a method for curing of radiation-curable compositions.

The substrates usable for application of coating materials, printing inks and adhesives can be various substrates such as papers, woods, metals and plastics, but the composition of the present invention is especially preferably applicable to plastics substrates as mentioned above.

BEST MODE FOR CARRYING OUT THE INVENTION

The present invention will be explained in more detail by the following examples, wherein "%" means % by weight and "part" means part by weight.

In Examples 1–15, refractive index was measured using Abbe refractometer, and specific gravity was measured in accordance with JISK-6835. The refractive index and the specific gravity were values at 25° C. $^1$H-NMR and $^{13}$C-NMR were measured using Model JNM-EX270 manufactured by Nihon Denshi Co., Ltd., and IR was measured using FT-IR of Model MAGNA750II manufactured by Nikorey Co., Ltd.

EXAMPLE 1

152 Grams (1.0 mol) of 3,4,5,6-tetrahydrophthalic anhydride and 200 g of toluene were charged in a flask equipped with a stirrer, a condenser tube and a water separator (Dean Stark Trap) and heated to 50° C. to dissolve the acid anhydride in toluene. Then, 61.1 g (1.0 mol) of 2-aminoethanol was added thereto dropwise over a period of 10 minutes, and thereafter the produced water was subjected to azeotropic dehydration with stirring at 120° C. for 3 hours to remove 18 g of water.

After cooling to 40° C., 79.3 g (1.1 mol) of acrylic acid, 0.12 g of hydroquinone monomethyl ether and 7.5 g of sulfuric acid were added to the flask, and the produced water was subjected to azeotropic dehydration with stirring at 120° C. for 3 hours to remove 18 g of water.

After cooling, 200 g of a 10% aqueous NaOH solution was added to the reaction mixture, followed by stirring for 30 minutes. Thereafter, the reaction mixture was transferred to a separating funnel, and the aqueous phase was separated and removed, thereby to remove the synthetic catalyst and excess acrylic acid.

The reaction mixture subjected to washing with alkali and containing toluene was transferred to the flask, and the solvent was distilled off under reduced pressure to obtain 205 g of a compound represented by the following formula. This compound had a viscosity of 890 mPas/25° C., but gradually became solid when stored at room temperature (melting point 50° C.) The compound was a compound of the formula (2) in which $R_8$ and $R_9$ are H, and s=1, and this compound is called A-1. Data of identification of A-1 are shown below.

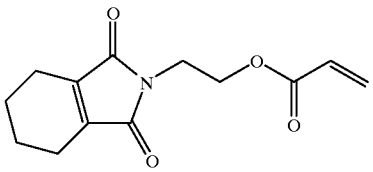

A-1 (white solid, m.p. 50° C., refractive index 1.517, specific gravity 1.199)

$^1$H-NMR (270 MHz, CDCl$_3$) δ 1.65–1.90(4H, —CH$_2$—C$\underline{H}_2$—C$\underline{H}_2$—CH$_2$—, m), 2.25–2.45(4H, —C$\underline{H}_2$—CH$_2$—CH$_2$—C$\underline{H}_2$—, m), 3.80(2H, —N—C$\underline{H}_2$—, t), 4.30(2H, —CO$_2$—C$\underline{H}_2$—, t), 5.85(1H, C$\underline{H}_2$=CH—, d), 6.10(1H, CH$_2$=C$\underline{H}$—, dd), 6.40(1H, C$\underline{H}_2$=CH—, d); $^{13}$C-NMR (67.8 MHz, CDCl$_3$) δ 19.9, 21.2, 36.3, 61.8, 127.9, 131.1, 141.6, 165.7, 170.6; IR(KBr) 2943, 1769, 1708, 1633, 1435, 1399, 1369, 1187, 1017, 986, 812 cm$^{-1}$.

EXAMPLE 2

The reaction and the after-treatment were carried out in the same manner as in Example 1, except that ethanolamine in Example 1 was changed to 75.1 g (1.0 mol) of 1-amino-2-propanol, thereby obtaining 220 g of a compound represented by the following formula. Viscosity of the compound was 1040 mPas/25° C.

The compound was a compound of the formula (2) in which $R_8$ was H and $R_9$ was CH$_3$, and s=1, and this compound is called A-2. Data of identification of A-2 are shown below.

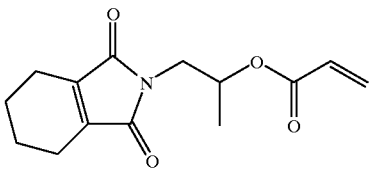

A-2 (light yellow liquid, viscosity 1040 mPas/25° C., refractive index 1.511, specific gravity 1.171).

$^1$H-NMR (270 MHz, CDCl$_3$) δ 1.25(3H, —C$\underline{H}_3$, d), 1.70–1.95(4H, —CH$_2$—C$\underline{H}_2$—C$\underline{H}_2$—CH$_2$—, m), 2.25–2.45(4H, —C$\underline{H}_2$—CH$_2$—CH$_2$—C$\underline{H}_2$—, m), 3.70(2H, —N—C$\underline{H}_2$—, m), 5.15(H, —CO$_2$—C$\underline{H}$—, m), 5.85(1H, C$\underline{H}_2$=CH—, d), 6.10(1H, CH$_2$=C$\underline{H}$—, dd), 6.40(1H, C$\underline{H}_2$=CH—, d); $^{13}$C-NMR (67.8 MHz, CDCl$_3$) δ17.9, 20.3, 21.6, 41.9, 69.3, 128.9, 131.2, 141.9, 165.9, 171.2; IR(neat) 2941, 1767, 1710, 1637, 1619, 1429, 1401, 1294, 1270, 1194, 1050, 1028, 911, 810 cm$^{-1}$.

EXAMPLE 3

The reaction and the after-treatment were carried out in the same manner as in Example 1, except that ethanolamine in Example 1 was changed to 105.1 g (1.0 mol) of 2-(2-aminoethoxy)ethanol, thereby obtaining 230 g of a compound represented by the following formula. Viscosity of the compound was 246 mPas/25° C.

The compound was a compound of the formula (2) in which $R_8$ and $R_9$ were H, and s=2, and this compound is called A-3. Data of identification of A-3 are shown below.

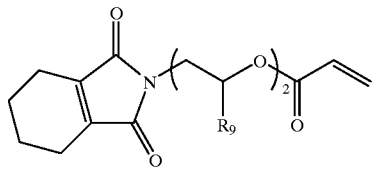

A-3 (light yellow liquid, viscosity 370 mPas/25° C., refractive index 1.511, specific gravity 1.190).

$^1$H-NMR (270 MHz, CDCl$_3$) δ 1.70–1.95(4H, —CH$_2$—C$\underline{H}_2$—C$\underline{H}_2$—CH$_2$—, m), 2.25–2.40(4H, —C$\underline{H}_2$—CH$_2$—CH$_2$—C$\underline{H}_2$—, m), 3.70(6H, —N—C$\underline{H}_2$, —OC$\underline{H}_2$—C$\underline{H}_2$—O—, m), 4.15(2H, —CO$_2$—C$\underline{H}_2$—, m), 5.85 (1H, C$\underline{H}_2$=CH—, d), 6.15(1H, CH$_2$=C$\underline{H}$—, dd), 6.45(1H, C$\underline{H}_2$=CH—, d); $^{13}$C-NMR (67.8 MHz, CDCl$_3$) δ 19.8, 21.2, 36.4, 63.5, 68.0, 68.1, 128.1, 130.7, 141.4, 165.8, 170.8; IR(neat) 2943, 2865, 1767, 1707, 1636, 1620, 1432, 1401, 1356, 1296, 1271, 1194, 1130, 1068, 1018, 987, 811 cm$^{-1}$.

EXAMPLE 4

The reaction and the after-treatment were carried out in the same manner as in Example 1, except that acrylic acid in Example 1 was changed to 86.1 g (1.0 mol) of methacrylic acid, thereby obtaining 210 g of a compound represented by the following formula. Viscosity of the compound was 395 mPas/25° C.

The compound was a compound of the formula (2) in which $R_8$ was CH$_3$ and $R_9$ was H, and s=1, and this compound is called M-1. Data of identification of M-1 are shown below.

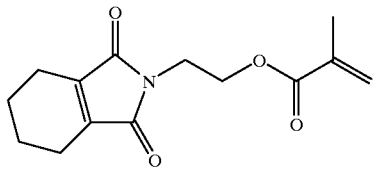

M-1 (light yellow liquid, viscosity 395 mPas/25° C., refractive index 1.514, specific gravity 1.175).

$^1$H-NMR (270 MHz, CDCl$_3$) δ 1.65–1.85(4H, —CH$_2$—C$\underline{H}_2$—C$\underline{H}_2$—CH$_2$—, m), 1.95(3H, CH$_2$=C-C$\underline{H}_3$, s), 2.25–2.45(4H, —C$\underline{H}_2$—CH$_2$—CH$_2$—C$\underline{H}_2$—, m), 3.80(2H, —N—C$\underline{H}_2$—, t), 4.30(2H, —CO$_2$—C$\underline{H}_2$—, t), 5.60(1H, C$\underline{H}_2$=C—, s), 6.10(1H, C$\underline{H}_2$=C—, s); $^{13}$C-NMR (67.8

MHz, CDCl$_3$) δ 18.0, 19.8, 21.1, 36.3, 62.0, 125.9, 135.7, 141.5, 166.8, 170.6; IR(neat) 2944, 1771, 1709, 1637, 1431, 1397, 1365, 1319, 1295, 1167, 1017, 993, 944, 816, 739, 716 cm$^{-1}$.

EXAMPLE 5

The reaction and the after-treatment were carried out in the same manner as in Example 2, except that acrylic acid in Example 2 was changed to 86.1 g (1.0 mol) of methacrylic acid, thereby obtaining 220 g of a compound represented by the following formula. Viscosity of the compound was 1202 mPas/25° C.

The compound was a compound of the formula (2) in which $R_8$ and $R_9$ were CH$_3$, and s=1, and this compound is called M-2. Data of identification of M-2 are shown below.

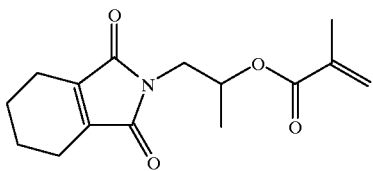

M-2 (light yellow liquid, viscosity 1202 mPas/25° C., refractive index 1.507, specific gravity 1.148).

$^1$H-NMR (270 MHz, CDCl$_3$) δ 1.25(3H, —CH$_3$, d), 1.70–1.90(4H, —CH$_2$—CH$_2$—CH$_2$—CH$_2$—, m), 1.95(3H, CH$_2$=C-CH$_3$, s), 2.25–2.45(4H, —CH$_2$—CH$_2$—CH$_2$—CH$_2$—, m), 3.70(2H, —N—CH$_2$—, m), 5.15(H, —CO$_2$—CH—, m), 5.60(1H, CH$_2$=C—, s), 6.10(1H, CH$_2$=C—, s);
$^{13}$C-NMR (67.8 MHz, CDCl$_3$) δ 17.4, 18.0, 19.8, 21.1, 41.4, 68.9, 125.6, 136.1, 141.4, 166.6, 170.6; IR(neat) 2939, 1767, 1713, 1637, 1450, 1430, 1400, 1384, 1322, 1292, 1169, 1127, 1029, 947, 912, 814, 744, 719 cm$^{-1}$.

EXAMPLE 6

The reaction and the after-treatment were carried out in the same manner as in Example 3, except that acrylic acid in Example 3 was changed to 86.1 g (1.0 mol) of methacrylic acid, thereby obtaining 225 g of a compound represented by the following formula. Viscosity of the compound was 246 mPas/25° C.

The compound was a compound of the formula (2) in which $R_8$ was CH$_3$ and $R_9$ was H, and s=2, and this compound is called M-3. Data of identification of M-3 are shown below.

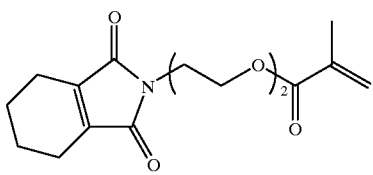

M-3 (light yellow liquid, viscosity 246 mPas/25° C., refractive index 1.508, specific gravity 1.167).

$^1$H-NMR (270 MHz, CDCl$_3$) δ 1.70–1.90(4H, —CH$_2$—CH$_2$—CH$_2$—CH$_2$—, m), 1.95(3H, CH$_2$=C—CH$_3$, s), 2.25–2.40(4H, —CH$_2$—CH$_2$—CH$_2$—CH$_2$—, m), 3.65(6H, —N—CH$_2$—, —OCH$_2$—CH$_2$—O—, m), 4.15(2H, —CO$_2$—CH$_2$—, m), 5.60(1H, CH$_2$=C—, s), 6.10(1H, CH$_2$=C—, s);
$^{13}$C-NMR (67.8 MHz, CDCl$_3$) δ 18.1, 19.8, 21.1, 36.5, 63.6, 67.9, 68.2, 125.4, 136.0, 141.3, 167.0, 170.8;
IR(neat) 2943, 2866, 1768, 1709, 1637, 1433, 1398, 1319, 1296, 1169, 1128, 1016, 945, 872, 816, 716 cm$^{-1}$.

EXAMPLE 7

50 Grams of A-1, 47.5 g of propylene glycol monomethyl ether acetate and 2.5 g of 2,2'-azobis(2-methylbutyronitrile) were charged in a flak equipped with a stirrer, a thermometer and a condenser tube at room temperature, to perform uniform dissolution. Then, the solution was heated and stirred at 85° C. for 2 hours and at 95° C. for 1 hour. After the reaction, substantially no monomer remained.

5 Grams of toluene was added to 10 g of the resulting viscous liquid containing a polymer, followed by adding dropwise the liquid little by little to 500 ml of methanol strongly stirred in a 1 liter beaker, and a solid precipitated in methanol was filtered off. Then, the solid was subjected to solvent drying under reduced pressure to obtain 3.2 g of a polymer. This is called P-1. Data of identification of P-1 are shown below.

P-1 (white solid) solution viscosity 95 mPas/25° C. (50 wt % toluene solution), molecular weight (Mn=6500, Mw=32100).

$^1$H-NMR (270 MHz, CDCl$_3$) δ 1.40–1.90(6H, br m), 2.10–2.45(5H, br m), 3.50–3.80(2H, br m), 3.90–4.40(2H, br m);
$^{13}$C-NMR (67.8 MHz, CDCl$_3$) δ 19.9, 21.3, 36.1, 36.4, 41.2, 61.7, 141.5, 170.6, 174.0;
IR(KBr) 2944, 1739, 1707, 1432, 1398, 1320, 1245, 1159, 1076, 1015, 945, 739, 716 cm$^{-1}$.

EXAMPLE 8

Polymerization was carried out in the same manner as in Example 7, except that 25 g (0.25 mol) of methyl methacrylate (hereinafter referred to as "MMA") and 25 g (0.10 mol) of A-1 were used in place of 50 g of A-1 in Example 7. After the reaction, substantially no monomer remained.

Purification was carried out in the same manner as in Example 7 to obtain 3.5 g of a polymer. This is called P-2. Data of identification of P-2 are shown below. The ratio of A-1 and MMA in the polymer obtained by $^1$H-NMR was A-1: MMA=2.9:7.1 (molar ratio).

P-2 (white solid), solution viscosity 172 mPas/25° C. (50 wt % toluene solution), molecular weight (Mn=5600, Mw=16200).

$^1$H-NMR (270 MHz, CDCl$_3$) δ 0.80–1.30 (br m), 1.40–2.20 (br m), 2.25–2.45 (br m), 3.45–3.85 (br m), 3.95–4.30 (br m);
$^{13}$C-NMR (67.8 MHz, CDCl$_3$) δ 16.5, 17.8, 20.0, 21.3, 35.9, 44.5, 44.9, 51.7, 54.4, 61.8, 141.7, 170.7, 176.8, 177.8;
IR(KBr) 2950, 1734, 1709, 1434, 1399, 1243, 1149, 1078, 991, 945, 748, 716 cm$^{-1}$.

EXAMPLE 9

Polymerization was carried out in the same manner as in Example 8, except that 25 g (0.095 mol) of A-2 was used in place of 25 g of A-1 in Example 8. After the reaction, substantially no monomer remained.

Purification was carried out in the same manner as in Example 7 to obtain 3.5 g of a polymer. This is called P-3. Data of identification of P-3 are shown below. The ratio of A-2 and MNA in the polymer obtained by $^1$H-NMR was A-2: MMA 2.8:7.2 (molar ratio).

P-3 (white solid) solution viscosity 451 mPas/25° C. (50 wt % toluene solution), molecular weight (Mn=8000, Mw=24100).

$^1$H-NMR (270 MHz, CDCl$_3$) δ 0.75–1.35 (br m), 1.40–2.20 (br m), 2.25–2.45 (br m), 3.40–3.80 (br m), 4.80–5.20 (br m);
$^{13}$C-NMR (67.8 MHz, CDCl$_3$) δ 16.5, 17.3, 17.5, 18.7, 19.9, 21.3, 41.3, 44.5, 44.8, 51.7, 54.3, 68.9, 141.5, 170.6, 177.8, 178.0;

IR(KBr) 2991, 2949, 1733, 1712, 1434, 1402, 1385, 1243, 1149, 1033, 989, 912, 746, 717 cm-1.

EXAMPLE 10

Polymerization was carried out in the same manner as in Example 8, except that 25 g (0.085 mol) of A-3 was used in place of 25 g of A-1 in Example 8. After the reaction, substantially no monomer remained.

Purification was carried out in the same manner as in Example 7 to obtain 3.9 g of a polymer. This is called P-4. Data of identification of P-4 are shown below. The ratio of A-3 and MMA in the polymer obtained by $^1$H-NMR was A-3: MMA 2.2:7.8 (molar ratio).

P-4 (white solid) solution viscosity 373 mPas/25° C. (50 wt % toluene solution), molecular weight (Mn=7500, Mw=24700).

$^1$H-NMR (270 MHz, CDCl$_3$) δ 0.80–1.30 (br m), 1.40–2.20 (br m), 2.25–2.45 (br m), 3.50–3.85 (br m), 4.00–4.30 (br m);

$^{13}$C-NMR (67.8 MHz, CDCl$_3$) δ 16.4, 17.7, 18.6, 19.9, 21.2, 36.6, 44.4, 44.8, 51.7, 54.2, 63.4, 68.0, 141.5, 170.9, 176.8, 177.7;

IR(KBr) 2951, 1734, 1708, 1435, 1400, 1243, 1148, 1018, 989, 945, 843, 750, 716 cm-1.

EXAMPLE 11

Polymerization was carried out in the same manner as in Example 8, except that 25 g (0.095 mol) of M-1 was used in place of 25 g of A-1 in Example 8. After the reaction, substantially no monomer remained.

Purification was carried out in the same manner as in Example 7 to obtain 4.1 g of a polymer. This is called P-5. Data of identification of P-5 are shown below. The ratio of M-1 and MMA in the polymer obtained by $^1$H-NMR was M-1: MMA 2.9:7.1 (molar ratio).

P-5 (white solid) solution viscosity 663 mPas/25° C. (50 wt % toluene solution), molecular weight (Mn=6300, Mw=17900).

$^1$H-NMR (270 MHz, CDCl$_3$) δ 0.70–1.50 (br m), 1.65–2.20 (br m), 2.25–2.45 (br m), 3.50–3.90 (br m), 3.95–4.30 (br m);

$^{13}$C-NMR (67.8 MHz, CDCl$_3$) δ 16.4, 18.6, 19.9, 21.2, 35.7, 44.4, 44.8, 45.4, 50.6, 54.3, 62.1, 141.7, 170.5, 176.8, 177.7;

IR(KBr) 2993, 2950, 1732, 1709, 1485, 1434, 1399, 1362, 1271, 1242, 1191, 1148, 1076, 993, 945, 748, 716 cm$^{-1}$.

EXAMPLE 12

Polymerization was carried out in the same manner as in Example 8, except that 25 g (0.195 mol) of butyl acrylate (hereinafter referred to as "BA") was used in place of 25 g of MMA in Example 8. After the reaction, substantially no monomer remained.

5 Grams of toluene was added to 10 g of the resulting viscous liquid containing a polymer, followed by adding dropwise the liquid little by little to 500 ml of methanol strongly stirred in a 1 liter beaker, but no solid was precipitated in methanol, and when stirring was stopped, a viscous liquid retained at the bottom of the beaker. The viscous liquid was subjected to solvent drying under reduced pressure to obtain 1.2 g of a polymer. This is called P-6. Data of identification of P-6 are shown below. The ratio of A-1 and BA in the polymer obtained by $^1$H-NMR was A-1: BA=3.3:6.7 (molar ratio).

P-6 (viscous liquid) solution viscosity 63 mPas/25° C. (50 wt % toluene solution), molecular weight (Mn=9800, Mw=41900).

$^1$H-NMR (270 MHz, CDCl$_3$) δ 0.80–1.05 (br m), 1.20–2.15 (br m), 2.15–2.45 (br m), 3.60–3.85 (br m), 3.85–4.40 (br m);

$^{13}$C-NMR (67.8MHz, CDCl$_3$) δ 13.7, 19.1, 20.0, 21.3, 30.6, 36.2, 36.4, 41.4, 61.8, 64.4, 141.6, 170.6, 174.0, 174.4;

IR(KBr) 2959, 2874, 1735, 1710, 1433, 1398, 1248, 1164, 1119, 1063, 1016, 945, 739, 721 cm$^{-1}$.

EXAMPLE 13

Polymerization was carried out in the same manner as in Example 8, except that 25 g (0.240 mol) of styrene (hereinafter referred to as "St") was used in place of 25 g of MMA in Example 8. After the reaction, substantially no monomer remained.

Purification was carried out in the same manner as in Example 7 to obtain 3.9 g of a polymer. This is called P-7. Data of identification of P-7 are shown below. The ratio of A-1 and St in the polymer obtained by $^1$H-NMR was A-1: St=2.9:7.1 (molar ratio).

P-7 (white solid) solution viscosity 92 mPas/25° C. (50 wt % toluene solution), molecular weight (Mn=6600, Mw=22700).

$^1$H-NMR (270 MHz, CDCl$_3$) δ 0.80–2.00 (br m), 2.20–2.45 (br m), 3.30–4.20 (br m), 6.40–7.40 (br m);

$^{13}$C-NMR (67.8 MHz, CDCl$_3$) δ 19.9, 21.2, 36.1, 40.8, 60.9, 125.2, 125.9, 128.0, 128.1, 129.0, 141.5, 170.5, 175.2;

IR(KBr) 3026, 2934, 1735, 1709, 1494, 1452, 1432, 1397, 1370, 1244, 1152, 1113, 1074, 1017, 945, 762, 701 cm$^{-1}$.

EXAMPLE 14

Polymerization was carried out in the same manner as in Example 8, except that 25 g of A-1 was changed to 45 g (0.181 mol), 5 g (0.039 mol) of BA was used in place of MMA, propylene glycol monomethyl ether acetate was changed to 49 g, and 2,2'-azobis(2-methylbutyronitrile) was changed to 1.0 g. After the reaction, substantially no monomer remained.

Purification was carried out in the same manner as in Example 7 to obtain 2.0 g of a polymer. This is called P-8. Data of identification of P-8 are shown below. The ratio of A-1 and BA in the polymer obtained by $^1$H-NMR was A-1: BA=8.2:1.8 (molar ratio).

Solution viscosity 138 mPas/25° C. (50 wt % toluene solution), molecular weight (Mn=8200, Mw=33800).

$^1$H-NMR (270 MHz, CDCl$_3$) δ 0.85–1.05 (br m), 1.20–2.10 (br m), 2.10–2.55 (br m), 3.60–3.85 (br m), 3.85–4.40 (br m);

$^{13}$C-NMR (67.8 MHz, CDCl$_3$) δ 13.7, 19.0, 20.0, 21.2, 30.5, 36.1, 36.4, 41.2, 61.7, 64.3, 141.5, 170.6, 174.0;

IR(KBr) 2943, 2864, 1738, 1706, 1432, 1398, 1321, 1244, 1160, 1114, 1077, 1015, 944, 876, 824, 739, 715 cm$^{-1}$.

EXAMPLE 15

Polymerization was carried out in the same manner as in Example 8, except that 20 g (0.076 mol) of M-1 was used in place of 25 g of A-1, the weight of MMA was changed to 30 g (0.300 mol), propylene glycol monomethyl ether acetate was changed to 50 g, and 2,2'-azobis(2-methylbutyronitrile) was changed to 0.25 g. After the reaction, substantially no monomer remained.

5 Grams of toluene was added to 10 g of the resulting viscous liquid containing a polymer, followed by adding dropwise the liquid little by little to 500 ml of methanol strongly stirred in a 1 liter beaker, but no solid was precipitated in methanol, and when stirring was stopped, a viscous liquid retained at the bottom of the beaker. The viscous liquid was subjected to solvent drying under reduced pressure to obtain 3.0 g of a polymer. This is called P-9. Data of identification of P-9 are shown below. The ratio of M-1 and MMA in the polymer obtained by $^1$H-NMR was M-1:MMA=2.0:8.0 (molar ratio).

Solution viscosity 644 mPas/25° C. (50 wt % toluene solution), molecular weight (Mn=26200, Mw=70800).

$^1$H-NMR (270 MHz, CDCl$_3$) δ 0.70–1.50 (br m), 1.65–2.15 (br m), 2.25–2.60 (br m), 3.50–3.70 (br m), 3.70–3.90 (br m), 3.95–4.20 (br m);

$^{13}$C-NMR (67.8 MHz, CDCl$_3$) δ 16.3, 18.6, 19.9, 21.2, 35.6, 44.4, 44.8, 51.7, 52.5, 54.3, 62.1, 141.6, 170.7, 176.9, 177.8, 178.1;

IR(KBr) 2994, 2949, 1734, 1709, 1485, 1434, 1399, 1362, 1271, 1243, 1192, 1147, 1076, 993, 966, 945, 843, 748, 716 cm$^{-1}$.

EXAMPLE 16

70 Parts of acrylate A-1 obtained in Example 1 and 30 parts of a mixture of pentaacrylate of dipentaerythritol (about 20% by weight) and hexaacrylate of dipentaerythritol (about 80% by weight) (Aronix M-400 manufactured by Toagosei Co., Ltd.) were mixed by conventional method to obtain a radiation-curable composition.

The resulting composition was evaluated on curability, weather resistance, abrasion resistance and adhesiveness by the following methods. The results are shown in Table 2.

Curability:

The resulting composition was coated at a thickness of 10μ on a Bonderite steel sheet (PB-144 manufactured by Japan Test Panel Co., Ltd.) as a substrate, and this was passed under a 120 W/cm condensing type high pressure mercury lamp (one lamp) at a conveyor speed of 5 m/min. The curability was evaluated in terms of the number of passing before the surface became tack-free.

Weather resistance:

The resulting composition was coated at a thickness of 10μ on a white PVC sheet manufactured by Japan Test Panel Co., Ltd. as a substrate, and this was passed under a 120 W/cm condensing type high pressure mercury lamp (one lamp, height: 10 cm)) at a conveyor speed of 5 m/min. The composition cured until the surface became tack-free was employed as a test specimen.

The test specimen was exposed to wetting conditions (100%RH/40° C.) for 6 hours and irradiation conditions (30 W/m$^2$/40° C.) for 6 hours alternately for 500 hours using a dew panel light control weatherometer DPWL-5R manufactured by Suga Tester Co., Ltd. as an accelerated exposure tester. Change in appearance was visually examined, and discoloration was evaluated by a differential calorimeter Sigma 80 manufactured by Nihon Denshoku Co., Ltd. In Table 2, the symbols "○", "Δ", and "X" in the change of appearance have the following meanings.

"○": No cracks occurred.

"Δ": Some cracks occurred.

"X": Cracks occurred on the whole of the coat.

Abrasion resistance:

The resulting composition was coated at a thickness of 10μ on a polycarbonate sheet manufactured by Japan Test Panel Co., Ltd. as a substrate, and this was passed under a 120 W/cm condensing type high pressure mercury lamp (one lamp, height: 10 cm)) at a conveyor speed of 5 m/min. The composition cured until the surface became tack-free was employed as a test specimen.

A steel wool of #000 was attached to a tip of a cylinder of 25 mm in diameter, and allowed to contact with the cured coat of the test specimen placed horizontally and rotated five times (20 rpm) under a load of 1.0 kg. Degree of flawing was visually examined. In Table 2, the symbols "⊙", "○", "Δ", and "X" have the following meanings.

"⊙": No flaws were caused on the surface of the specimen.

"○": Some flaws were caused on the surface of the specimen.

"Δ": Considerable flaws were caused on the surface of the specimen.

"X": The surface of the substrate at the flaw portions was exposed.

Adhesiveness:

The same test specimen as used in the abrasion resistance test was subjected to the cellophane tape peeling test in accordance with JIS K-5400. The adhesion was evaluated in terms of the number of the remaining squares per 100 squares according to the following criteria. The substrate was a polycarbonate sheet manufactured by Japan Test Panel Co., Ltd.

"○": More than 90 squares.

"Δ": 10–90 squares.

"X": Less than 10 squares.

Odor:

The cured coat of the composition was smelled just after curing, and evaluation was conducted by the following criteria.

"○": Substantially no odor.

"Δ": Slight odor.

"X": Considerable odor.

"XX": Strong odor.

EXAMPLES 17–21

Radiation-curable compositions were prepared in the same manner as in Example 16 using A-1 to A-3 obtained in Examples 1–3, except for using the ingredients and the formulations as shown in Table 1.

The resulting compositions were evaluated in the same manner as in Example 16. The results are shown in Table 2.

TABLE 1

| Example | A-1 | A-2 | A-3 | M-400[1] | M-1600[2] | M-8060[3] | M-309[4] | Irg 184[5] | Tinuvin 144[6] | Tinuvin 328[7] |
|---|---|---|---|---|---|---|---|---|---|---|
| 16 | 70 | — | — | 30 | — | — | — | — | — | — |
| 17 | — | 30 | — | 60 | — | — | 10 | 0.5 | — | — |
| 18 | — | — | 80 | — | 20 | — | — | — | — | — |
| 19 | 40 | — | — | 30 | — | 30 | — | — | 0.2 | 0.2 |
| 20 | 20 | — | — | 60 | 20 | — | — | — | 0.5 | 0.5 |
| 21 | — | 30 | — | — | 30 | — | 40 | — | 0.5 | 0.5 |

TABLE 1-continued

| Example | A-1 | A-2 | A-3 | M-400[1] | M-1600[2] | M-8060[3] | M-309[4] | Irg 184[5] | Tinuvin 144[6] | Tinuvin 328[7] |
|---|---|---|---|---|---|---|---|---|---|---|

[1]M-400: Aronix M-400 manufactured by Toagosei Co., Ltd., a mixture of pentaacrylate of dipentaerythritol (about 20% by weight) and hexaacrylate of dipentaerythritol (about 80% by weight).
[2]M-1600: Aronix M-1600 manufactured by Toagosei Co., Ltd., non-yellowing urethane diacrylate.
[3]M-8060: Aronix M-8060 manufactured by Toagosei Co., Ltd., polyester polyacrylate.
[4]M-309: Aronix M-309 manufactured by Toagosei Co., Ltd., trimethylolpropane triacrylate.
[5]Irg 184: Irgacure 184 manufactured by Ciba-Geigy Corp., hydroxycyclohexylacetophenone (photopolymerization initiator).
[6]Tinuvin 144: Tinuvin 144 [bis(1,2,2,6,6-pentamethyl-4-piperidyl 2-(3,5-di-t-butyl-4-hydroxybenzyl)-2-n-butylmalonate)] (light stabilizer) manufactured by Ciba-Geigy Corp.
[7]Tinuvin 328: Tinuvin 328 [2-(3,5-di-t-amyl-2-hydroxyphenyl)benzotriazole] (ultraviolet absorber) manufactured by Ciba-Geigy Corp.

TABLE 2

| Example | Curability (Number of passing) | Appearance | ΔE Color difference | Abrasion resistance | Adhesiveness | Odor |
|---|---|---|---|---|---|---|
| | | Weather resistance | | | | |
| 16 | 3 | ○ | 1.0 | ○ | ○ | ○ |
| 17 | 2 | ○ | 1.5 | ◉ | ○ | Δ |
| 18 | 3 | ○ | 0.8 | ○ | ○ | ○ |
| 19 | 2 | ○ | 1.1 | ◉ | ○ | ○ |
| 20 | 3 | ○ | 0.8 | ◉ | ○ | ○ |
| 21 | 4 | ○ | 0.5 | ◉ | ○ | ○ |

EXAMPLES 22–24

Radiation-curable compositions were prepared in the same manner as in Example 16 using M-1 to M-3 obtained in Examples 4–6, except for using the additives and the formulations as shown in Table 3.

The resulting compositions were evaluated in the same manner as in Example 16 on curability, abrasion resistance, adhesion and odor. The results are shown in Table 3. These compositions had the weather resistance similar to that of Examples 16–21.

TABLE 3

| Example | M-1 | M-2 | M-3 | M-400 | M-8060 | Curability (Number of passing) | Abrasion resistance | Adhesiveness | Odor |
|---|---|---|---|---|---|---|---|---|---|
| 22 | 50 | — | — | 50 | — | 2 | ○ | ○ | ○ |
| 23 | — | 70 | — | 30 | — | 2 | ○ | ○ | ○ |
| 24 | — | — | 30 | — | 70 | 3 | ○ | ○ | ○ |

COMPARATIVE EXAMPLES 1–3

Radiation-curable compositions were prepared in the same manner as in Example 16, except for using the additives and the formulations as shown in Table 4.

The resulting compositions were evaluated in the same manner as in Example 16. The results are shown in Table 5.

TABLE 4

| Comparative Example | M-120[8] | Viscoat #190[9] | M-400 | M-1600 | M-8060 | M-309 | Irg 184 | Benzophenone | Tinuvin 144 | Tinuvin 328 |
|---|---|---|---|---|---|---|---|---|---|---|
| 1 | 80 | — | — | 20 | — | — | 1 | 1 | — | — |
| 2 | 40 | — | 30 | — | 30 | — | 2 | — | 0.5 | 0.5 |
| 3 | — | 30 | — | 30 | — | 40 | 2 | — | 0.5 | 0.5 |

[8]M-120: Aronix M-120 manufactured by Toagosei Co., Ltd., 2-ethylhexyl acrylate modified with 2 mols of ethylene oxide.
[9]Viscoat #190: Ethoxyethoxyethyl acrylate manufactured by Osaka Yuki Kagaku Co., Ltd.

TABLE 5

| Comparative Example | Curability (Number of passing) | Weather resistance | | Abrasion resistance | Adhesiveness | Odor |
|---|---|---|---|---|---|---|
| | | Appearance | ΔE Color difference | | | |
| 1 | 4 | x | 7.5 | Δ | Δ | xx |
| 2 | 5 | Δ | 3.2 | ○ | ○ | x |
| 3 | 4 | Δ | 3.6 | Δ | Δ | x |

TABLE 6

| Example | P-1 | P-2 | P-3 | P-4 | P-5 | P-6 | P-7 | P-8 | P-9 | M-305 | M-210 |
|---|---|---|---|---|---|---|---|---|---|---|---|
| 25 | 10 | — | — | — | — | — | — | — | — | 90 | — |
| 26 | 10 | — | — | — | — | — | — | — | — | — | 90 |
| 27 | — | 10 | — | — | — | — | — | — | — | 90 | — |
| 28 | — | — | 10 | — | — | — | — | — | — | 90 | — |
| 29 | — | — | — | 10 | — | — | — | — | — | 90 | — |
| 30 | — | — | — | — | 10 | — | — | — | — | 90 | — |
| 31 | — | — | — | — | — | 10 | — | — | — | 90 | — |
| 32 | — | — | — | — | — | — | 10 | — | — | 90 | — |
| 33 | — | — | — | — | — | — | — | 10 | — | 90 | — |
| 34 | — | — | — | — | — | — | — | — | 10 | 90 | — |

EXAMPLES 25–32

One gram of P-1 was added to 9 g of Aronix M-305 manufactured by Toagosei Co., Ltd. (pentaerythritol triacrylate), followed by stirring at 80° C. to dissolve P-1 to obtain a radiation-curable composition (Example 25).

Furthermore, radiation-curable compositions were prepared in the same manner as in Example 25, except for changing the formulations to those shown in Table 6 (Examples 26–32).

The resulting compositions were evaluated on curability, solvent resistance, pencil hardness and odor by the following methods. The results are shown in Table 7. These compositions had the weather resistance similar to that of Examples 16–21.

Curability:

The composition was coated on a phosphoric acid-treated iron sheet (PB144 manufactured by Japan Test Panel Co., Ltd.) by bar coater #10, and cured by irradiation with ultraviolet rays under the same conditions as in Example 16, except that the lamp output was changed from 120 W/cm to 80 W/cm, and the conveyor speed was changed from 5 m/min to 10 m/min. The curability was evaluated in terms of the number of passing as in Example 16.

Solvent resistance:

The cured coat was rubbed with a swab impregnated with acetone, and the solvent resistance was evaluated in terms of the number of rubbing before the coat was whitened or broken.

Pencil hardness:

This was measured in accordance with JIS K-5400.

Odor:

The cured coat of the composition was smelled just after curing, and evaluation was conducted by the following criteria.

"○": Substantially no odor.
"Δ": Slight odor.
"X": Considerable odor.
"XX": Strong odor.

TABLE 7

| Example | Curability (Number of passing) | Solvent resistance | Pencil hardness | Odor |
|---|---|---|---|---|
| 25 | 4 | >50 | 3H | ○ |
| 26 | 2 | >50 | 3H | ○ |
| 27 | 5 | >50 | 2H | ○ |
| 28 | 6 | >50 | 2H | ○ |
| 29 | 6 | >50 | 2H | ○ |
| 30 | 6 | >50 | 3H | ○ |
| 31 | 8 | >50 | 2H | ○ |
| 32 | 7 | >50 | 2H | ○ |
| 33 | 5 | >50 | 3H | ○ |
| 34 | 5 | >50 | 3H | ○ |

COMPARATIVE EXAMPLE 4

Radiation-curable compositions were prepared in the same manner as in Example 16, except for using the additives and the formulations as shown in Table 8.

The resulting compositions were evaluated in the same manner as in Example 25. The results are shown in Table 8.

TABLE 8

| Comparative Example | M-305 | Irg 651[10] | Curability (Number of passing) | Solvent resistance | Pencil Hardness | Odor |
|---|---|---|---|---|---|---|
| 4 | 100 | 1 | 3 | >50 | 3H | x |

[10]Irg 651: Irgacure 651, benzildimethyl ketal, manufactured by Ciba Specialty Chemicals Co., Ltd.

INDUSTRIAL APPLICABILITY

The imido (meth)acrylate of the present invention can be easily produced, is readily cured by irradiation with radiations, and, furthermore, has excellent curability without photopolymerization initiator even when it is cured by irradiation with ultraviolet rays. Moreover, cured products have substantially no odor and have excellent weather resistance, abrasion resistance and adhesiveness.

The radiation-curable compositions containing the imido (meth)acrylate of the present invention or a polymer containing the imido (meth)acrylate as a constitutive monomer have the above-mentioned properties and can be utilized as coating agents, adhesives and molding materials with excellent properties, and can be utilized in paint, adhesive and plastic molding techniques.

What is claimed is:

1. A radiation-curable composition which contains an imido (meth)acrylate represented by the following formula, and a (meth)acrylate having 2 or more (meth)acryloyl groups in one molecule:

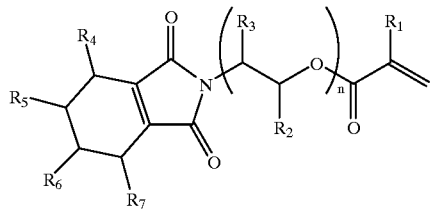

wherein $R_1$, $R_2$ and $R_3$ each represents H or $CH_3$, and $R_1$, $R_2$ and $R_3$ in one molecule may be the same or different, $R_4$–$R_7$ each represent H or $CH_mH_{2m+1}(m=1–6)$, and $R_4$–$R_7$ in one molecule may be the same or different, and $n=1–4$.

2. A radiation-curable composition according to claim 1, wherein the constitutional ratio of the imido (meth)acrylate and the (meth)acrylate is 5–95% by weight: 95–5% by weight.

3. A radiation-curable composition according to claim 1, wherein $R_3$–$R_7$ of the imido (meth)acrylate each represents H.

4. An ultraviolet radiation-curable composition which contains an imido (meth)acrylate represented by the following formula:

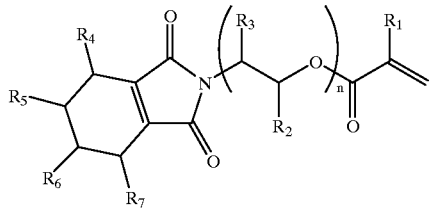

wherein $R_1$, $R_2$ and $R_3$ each represents H or $CH_3$, and $R_1$, $R_2$ and $R_3$ in one molecule may be the same or different, $R_4$–$R_7$ each represents H or $C_mH_{2m+1}(m=1–6)$, and $R_4$–$R_7$ in one molecule may be the same or different, and $n=1–4$; and a (meth)acrylate having 2 or more (meth)acryloyl groups in one molecule, and substantially free of a photo initiator.

5. An ultraviolet radiation-curable composition according to claim 3, wherein $R_3$–$R_7$ of the imido (meth)acrylate each represents H.

6. An ultraviolet radiation-curable composition according to claim 3, wherein the constitutional ratio of the imido (meth)acrylate, and the (meth)acrylate is 5–95% by weight: 95–5% by weight.

* * * * *